(12) United States Patent
Wang et al.

(10) Patent No.: US 6,924,484 B1
(45) Date of Patent: Aug. 2, 2005

(54) VOID CHARACTERIZATION IN METAL INTERCONNECT STRUCTURES USING X-RAY EMISSION ANALYSES

(75) Inventors: Ying Wang, San Jose, CA (US); Anne Testoni, Bolton, MA (US)

(73) Assignee: KLA-Tencor Corporation, Milpitas, CA (US)

(*) Notice: Subject to any disclaimer, the term of this patent is extended or adjusted under 35 U.S.C. 154(b) by 62 days.

(21) Appl. No.: 10/691,940

(22) Filed: Oct. 22, 2003

Related U.S. Application Data

(60) Provisional application No. 60/427,906, filed on Nov. 19, 2002.

(51) Int. Cl.[7] .................. G01N 23/223; H01J 37/153
(52) U.S. Cl. .............. 250/310; 250/492.2; 250/306; 250/307
(58) Field of Search ................ 250/310, 492.2, 250/306, 307

(56) References Cited

U.S. PATENT DOCUMENTS

| | | | |
|---|---|---|---|
| 5,877,498 A | * | 3/1999 | Sugimoto et al. ........... 250/310 |
| 5,900,645 A | | 5/1999 | Yamada |
| 6,351,516 B1 | | 2/2002 | Mazor et al. |

OTHER PUBLICATIONS

Amekura, Hiroshi et al., *X–Ray Emission Induced by 60 keV High–Flux Copper Negative–Ion Implantation*, Feb. 2001, Japan Society of Applied Physics.

Shaw, Judy B. et al., *Voids, Pits, and Copper*, Winter 2002, Yield Management Solutions: Cu/low Special Focus.

Testoni, A.L., *CuVA: Analyzing Voids in Cu Interconnects*, Jun. 20, 2002, KLA–Tencor Progress Report.

\* cited by examiner

*Primary Examiner*—Nikita Wells
(74) *Attorney, Agent, or Firm*—Beyer, Weaver & Thomas, LLP.

(57) ABSTRACT

Disclosed are methods and apparatus for characterizing a potential void or voids by analyzing the X-ray count of one or more emitted X-ray species as emitted from an interconnect structure under test in response to a impinging beam, such as an electron beam, directed towards the sample surface. For example, this analysis may be used to determine whether the structure (e.g., a contact, line or via) has one or more void(s). It may also he used to help determine where the void(s) are with respect to the interconnect structure. It may also be used to help determine other characteristics of the void(s) with respect to the interconnect structure such as the shape(s) and size(s) of the void(s). The analysis may also be used to help initially determine whether the structure under test is so out of specification that it cannot then be determined whether the structure has a defect of a particular type. This analysis can be used to evaluate the process variation of wafers.

52 Claims, 13 Drawing Sheets

Top View (401)

Side View (405)

Side View (419)

VOID CHARACTERIZATION IN METAL INTERCONNECT STRUCTURES USING X-RAY EMISSION ANALYSES

CROSS REFERENCE TO RELATED PATENT APPLICATION

This application claims priority to U.S. Provisional Application No. 60/427,906, filed Nov. 19, 2002, entitled VOID CHARACTERIZATION IN METAL INTERCONNECT STRUCTURES USING X-RAY EMISSION ANALYSES, which application is incorporated herein by reference it its entirety for all purposes.

FIELD OF THE INVENTION

The present invention relates generally to methods for characterizing voids within conductive interconnect structures of semiconductor devices. More specifically, the invention pertains to using X-ray emission analysis techniques to characterize voids within metal vias, contacts and lines of metal interconnect structures.

BACKGROUND OF THE INVENTION

Voids within metal interconnect structures, such as those in integrated circuits, can have different sizes, distributions and locations within the interconnect structures. For example, voids can range from "monster" voids occluding whole lines, vias or contacts with immediate yield impact, to small voids within lines, vias or contacts that impact the long-term reliability of the device. Voids can be uniformly distributed within a line, via or contact section or they can be localized in deep or shallow portions of a line, via or contact.

Void formation can stem from a number of different root causes. For example, a void can form during a metal film deposition process where there is poor step coverage, typically resulting in a slit shaped void in the middle of via or contact regions. A void can also form from the scratching of metal surfaces during chemical mechanical polishing (CMP) with subsequent metal deposition, typically resulting in a shallow, long void in the upper portion of a via and line. Other examples include voids caused during the high temperature annealing process of metal film and during trench and via etching. If one could characterize the size, distribution and location of voids, one could gain information about the root causes of the voids.

Traditionally, the only way to know the size, distribution and location of voids is by using destructive methods such as Focused Ion Beam (FIB) cross-sectioning techniques. Although these techniques can help verify the existence of voids, the sample is destroyed during the analysis. This is expensive for integrated circuit manufacturers since it means sacrificing product samples from the product line and often results in wasting product found to have no significant defects. Furthermore, FIB techniques are time consuming, which can cause downtime of the product line production. This can be an especially big problem if numerous scans on numerous wafers are needed to ensure void-free processing.

Accordingly, there is a need to characterize voids that may reside within integrated circuit product lines efficiently and without sacrificing valuable product.

SUMMARY

In general terms, the present invention provides methods and apparatus for characterizing a potential void or voids by analyzing the X-ray count of one or more emitted X-ray species as emitted from an interconnect structure under test in response to a impinging beam, such as an electron beam, directed towards the sample surface. For example, this analysis may be used to determine whether the structure (e.g., a contact, line or via) has one or more void(s). It may also be used to help determine where the void(s) are with respect to the interconnect structure. It may also be used to help determine other characteristics of the void(s) with respect to the interconnect structure such as the distribution and size(s) of the void(s). The analysis may also be used to help initially determine whether the structure under test is so out of specification that it cannot then be determined whether the structure has a defect of a particular type.

By directing a beam of appropriate energy toward the sample surface, a certain volume of the sample will generate X-rays. These X-rays will radiate from the volume within the sample and some of the X-rays will be emitted from the sample surface. These emitted X-rays are characteristic of composition of the sample. If the sample is comprised of an interconnect structure, such as a semiconductor device, the X-rays emitted from the sample will be characteristic of the interconnect structure, as well as the surrounding material.

In one embodiment, the sample is a copper semiconductor device surrounded by dielectric material. By detecting and collecting the copper K and copper L X-rays emitted from the sample, and by calculating various ratios of the intensities of emitted copper K and copper L X-rays, one can characterize the interconnect structure with respect to how deeply each of the X-rays penetrate the sample. Thus, by sampling another similar sample, but with void(s), one can determine where the void(s) are, how the void(s) are distributed and what size the void(s) are with respect to the copper interconnect structure. These techniques are described in detail further. One can also detect and collect X-ray emission from other elemental species emitted from the sample to implement similar analyses.

To improve the reliability of the results of these techniques, one can scan a number of samples, thereby allowing statistical analyses. These statistical analyses can include taking absolute values of the emitted X-rays, calculating the mean of X-ray emission for the various scans and calculating the standard deviations of X-ray emission for the various scans. One can also improve the reliability of results by including the X-ray emission data of species that are not part of the interconnect structure. For example, if a copper interconnect structure is surrounded by silicon dioxide, one can detect and collect the silicon Kα emission from the sample and use it to emphasize the variations of the Cu Lα and Cu Kα X-rays with respect to the copper interconnect surroundings.

In a specific implementation, the characterizing operation is based on collecting the characteristics X-rays of a first "non-voided" sample, collecting the characteristic X-rays of a second "known voided" sample, collecting the characteristic X-rays of third "unknown" sample and comparing the X-ray data from the three samples to determine the void characteristics of the third "unknown" sample. This is done by establishing rules for characteristic X-ray parameters and "binning" the X-ray data into a database. These techniques are described in detail further.

In one embodiment, the beam directed toward the sample to cause X-ray emission from the sample is an electron beam. In one aspect, the electron beam is preferably tightly focused, in that it is sufficiently focused to resolve X-ray emission differences between small features of interest in current semiconductor devices. In another aspect, the electron beam has preferably high enough energy to travel through the different layers of a typical semiconductor film stack.

In one embodiment, the electron beam can be rastered over a region of the sample so as to ensure sampling of the entire structure of interest. The rastering can also provide for more X-ray data to be collected over the structure of interest.

In another embodiment, the beam directed toward the sample to cause X-ray emission from the sample is a focused ion beam. In one aspect, the focused ion beam is sufficiently focused to resolve X-ray emission differences between small features of interest in current semiconductor devices. In another aspect, the focused ion beam has preferably high enough energy to travel through the different layers of a typical semiconductor film stack.

These and other features of the present invention will be presented in more detail in the following specification of the invention and the accompanying figures, which illustrate by way of example the principles of the invention.

DETAILED DESCRIPTION OF SPECIFIC EMBODIMENTS

Introduction

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, X-ray emission analyses involve characterizing the composition of a sample by exciting the atomic core electrons within a sample and analyzing the resulting emitted X-rays. In the present invention, excitement of the atomic core electrons is achieved by bombarding the sample with a focused electron beam (e-beam), although other techniques of inducing X-ray emission such as a focused ion beam can be used. Upon sample bombardment, a transfer of energy occurs which excite the atomic core electrons into different electronic energy levels. Once in this excited state, the atoms have two possible modes of relaxation: emission of X-rays, or emission of Auger electrons.

Figure 5:
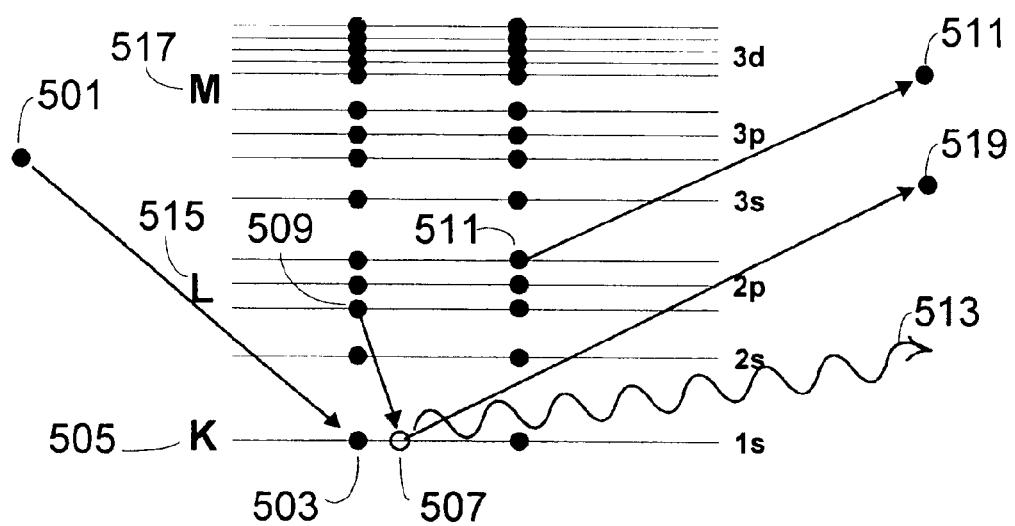
FIG. 5 is a diagram of a Bohr model of an atom showing electronic transitions during Auger electron emission and X-ray emission competing processes.

To illustrate these two possibilities, FIG. 5 illustrates a Bohr model of an atom with three electronic energy levels K, L and M (505, 515 and 517, respectively), with electrons in K having greater electronic binding energy than those in L, and electrons in L having greater binding energy than those in M. An incident electron 501 strikes an atom with enough energy to displace an atomic core electron 503, causing the ejection of a secondary electron 519 and producing a core hole or vacancy 507. With the vacancy in the core energy level, the atom is energetically unstable. The most probable stabilization mechanism is filling the vacancy with another electron in a higher energy level 509. That is, a second electron falls from a higher level into the vacancy with release of energy. The resulting energy may then be carried off by one of two mechanisms: Auger electron emission or X-ray emission. In Auger electron emission, the resulting energy is carried off when an Auger electron 511 from a higher energy level is ejected. In X-ray emission, the resulting energy is carried off in the form of emitted X-rays 513, leaving an ionized atom. Auger electron emission and X-ray emission are competitive processes.

The present invention pertains to the detection and analysis of X-ray emissions of a sample in accordance with above description. Each element has its own characteristic electronic energy configurations and its own characteristic X-ray emissions. For example, copper has two dominant characteristic X-ray emissions: a Lα emission emitted when an electron falls from the M electronic energy level into the L electronic energy level to fill the vacancy resulting from the L shell ionization, and a Kα emission formed when an electron falls from L electronic energy level to K electronic energy level to fill the vacancy resulting from K shell ionization. An energy spectrum of detected X-rays emitted from a sample containing different elements shows peaks characteristic of the elements present in the sample. The ratios of the intensities of X-ray peaks can provide a quantitative determination of surface and subsurface composition.

Figure 6:
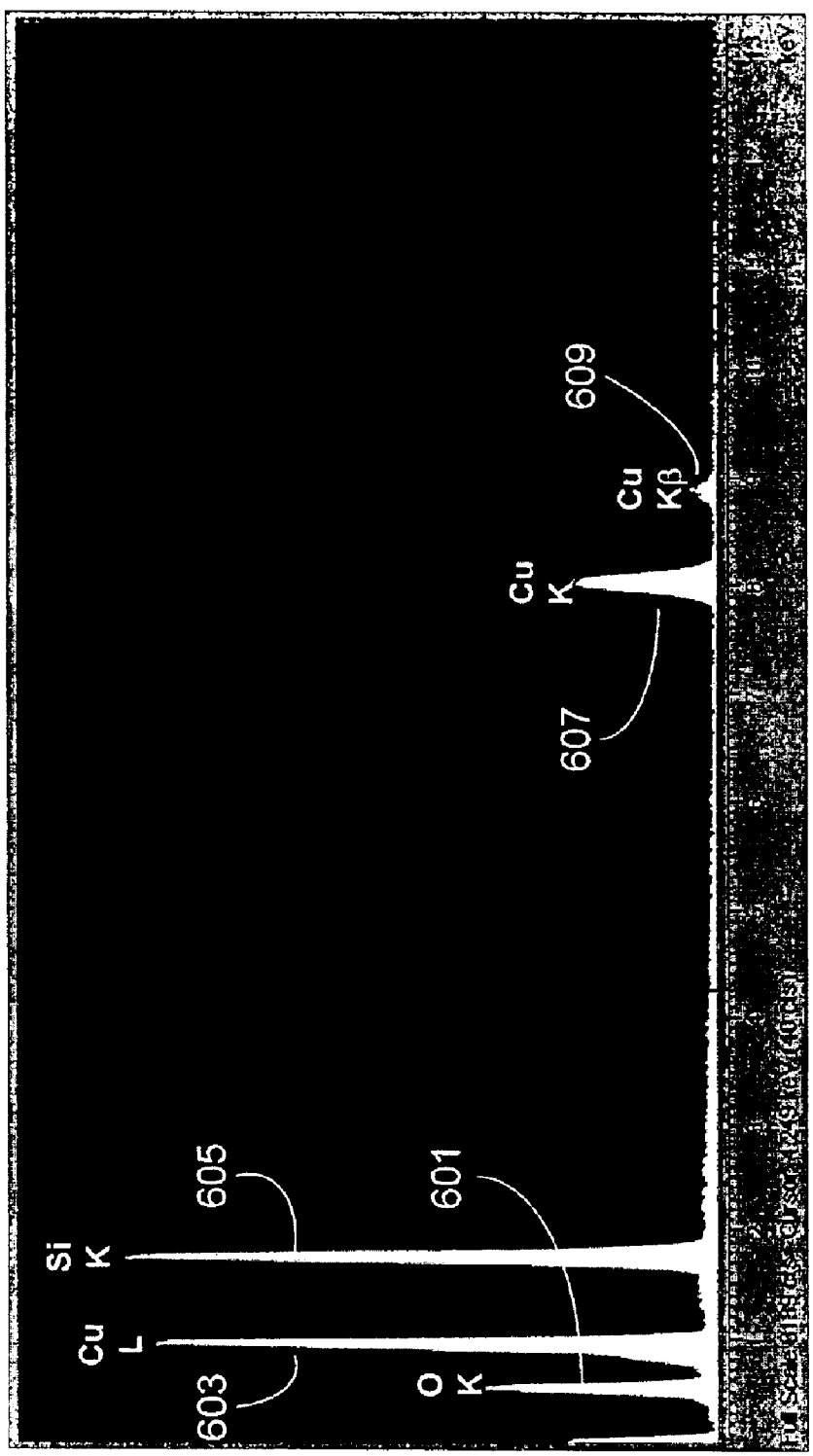
FIG. 6 is an X-ray emission spectrum from a copper semiconductor integrated device sample.

For example, FIG. 6 shows an X-ray emission spectrum from a copper interconnect structure in an integrated circuit. The horizontal axis represents energy in keV and the vertical axis is the relative intensity. The oxygen Kα (O Kα) peak 601 has an energy of about 0.525 keV. The copper Lα (Cu Lα) peak 603 has a larger intensity than O Kα and has an energy of about 0.93 keV. The silicon (Si Kα) peak 605 has an energy of about 1.74 keV. The copper Kα peak (Cu Kα) 607 has a lower intensity than the Cu Lα and Si Kα peaks; it has an energy of about 8.04 keV. The small intensity peak to the right of 607 is copper Kβ peak (Cu Kβ), which has an energy of about 8.90 keV. The relative intensities of the peaks in this X-ray spectrum can be compared to spectra of the pure elements or other samples of known composition to determine the quantitative composition of elements in the sample.

In a preferred embodiment of the invention, X-ray emission is induced with an e-beam. In general, when an e-beam bombards the surface of a sample, a portion of the sample, the interaction volume, is determined by the kinetic energy of the bombarding electrons. While not wishing to be bound by theory, the shape of the interaction volume is often described as "teardrop" or "pear" for those skilled in the art. It is worth noting, however, that the interaction volume for any particular sampling can vary from a vertically elongated teardrop, to a hemisphere-like teardrop, to a horizontally squeezed teardrop, depending on the composition of the sample and the e-beam energy. For simplicity and clarity, discussions and illustrations herein will describe interaction volumes as "teardrop" shaped to help explain certain aspects of the invention. It should be noted, however, that the present invention is not limited to any particular shape or size of interaction volume.

Figure 2A:
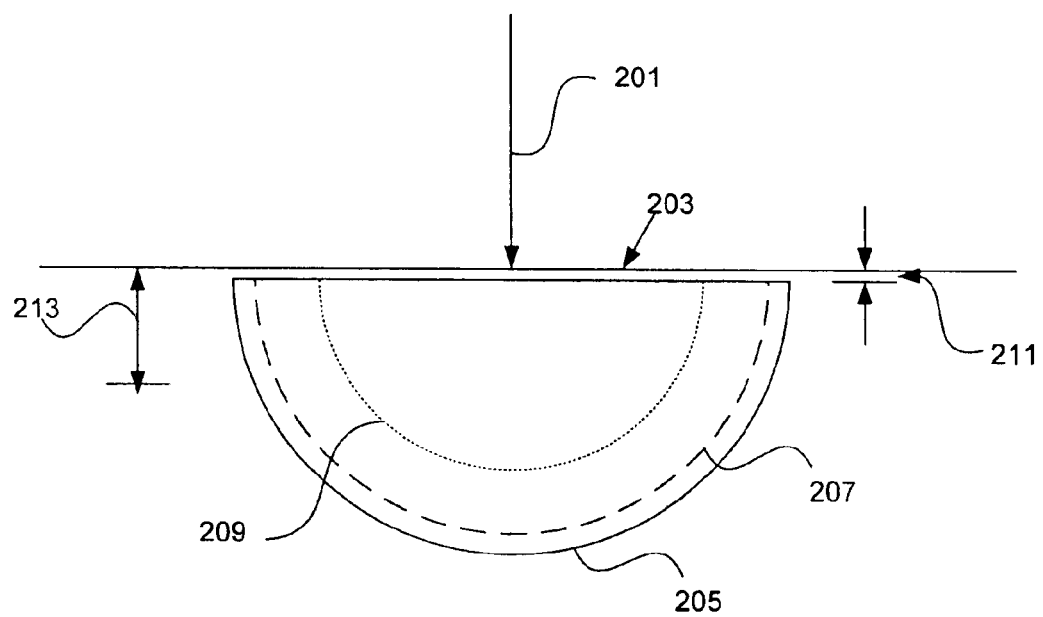
FIG. 2A illustrates a cross section of copper-cobalt alloy sample with an electron beam incident upon a sample showing interaction volume and sampling volume within the sample.

As a result of the e-beam 201 bombardment, regions of sample 203 will electronically excite atoms within the sample 203 and generate X-rays characteristic of these atomic elements. The regions that generate X-rays are referred to as x-ray excitation volumes. In FIG. 2A, for example, Cu Lα excitation volume 207 and Cu Kα excitation volume 209 are depicted. Note that Cu Lα x-ray excitation volume 207 and Cu Kα x-ray excitation volume 209 are smaller than interaction volume 205.

Once X-rays generated in Cu Lα excitation volume 207 and Cu Kα excitation volume 209, some of the generated X-rays have enough energy to penetrate through the thickness of the sample 203 towards the surface and are emitted from the surface of the sample 203. These emitted X-rays (not shown) can be detected by a detector (not shown) and analyzed, for example, by X-ray emission spectroscopy techniques as described above. Note that due to self-absorption, not all the X-rays generated within sample 203 have enough energy to penetrate though the thickness of the sample 203 to reach the surface and thereby be detected by a detector. The x-ray emission that escapes from the surface and reaches the detector is often from a smaller region than the x-ray excitation volume. This smaller volume is called x-ray sampling volume.

For a comprehensive discussion regarding concepts of electron-material interaction, interaction volume and X-ray sampling volume, and x-ray excitation volume can be found, refer to the book Scanning Electron Microscopy and X-ray Microanalysis, Second Edition, Joseph I. Goldstein, et al. Plenum Press, New York and London, 1992.

Figure 2B:
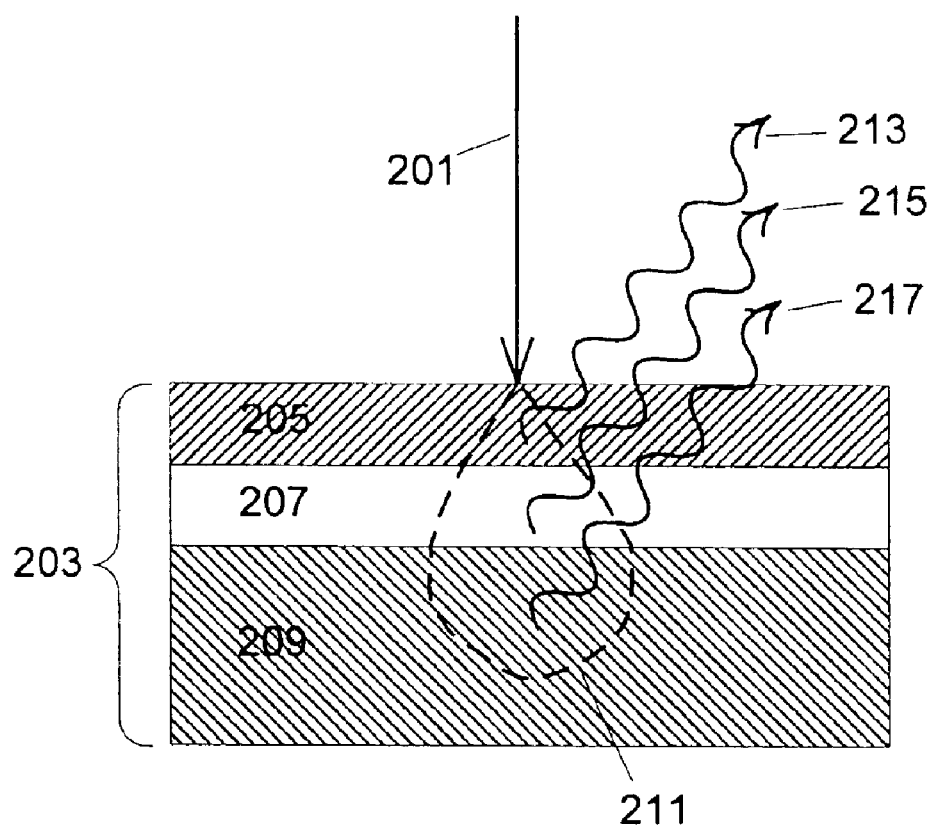
FIG. 2B illustrates a cross section of a semiconductor sample with an electron beam incident upon a sample, resulting in X-rays being emitted by various layers of the sample material.

As mentioned previously, the present invention is particularly useful for analyzing voids within integrated circuits. For an integrated circuit sample containing dielectric material such as silicon dioxide and regions of metal conductor such as copper vias or lines, For example, FIG. 2B illustrates a cross section view of a focused e-beam 201 bombarding a sample integrated circuit stack 203 composed of layers of copper 205 and dielectric material 207 over a silicon substrate 209. The electron interaction volume is depicted as teardrop 211. Some of the X-rays generated within the sampling volume 211 from the copper, dielectric and silicon layers in the stack have enough energy to penetrate through the stack 203 so that they are emitted from the surface of the sample. For example, X-rays 213, 215 and 217 penetrate from different layers of the stack 203 penetrate through the stack and are emitted from the surface of the sample.

In preferred embodiments, the incident e-beam will have a high enough energy to travel through the different layers of interest of the film stack and to generate X-rays in the sample structure of interest. This e-beam energy will depend on the sample composition and thickness and on how deep the structures of interest lie. To analyze most structures of interest, such as copper vias or contacts and lines of the uppermost stack of a typical copper integrated circuit sample, this e-beam energy is preferably no less than about 15 keV.

In preferred embodiments, the diameter of the incident e-beam is tightly focused over the structure of interest. Features of interest in integrated circuits in copper vias are very small—for example, currently as small as 150 nanometers (nm) in diameter. Therefore, to characterize such small features, the e-beam diameter is preferably sufficiently focused to resolve them. In some embodiments, the e-beam can be rastered over the region of interest to collect data. In other embodiments, the e-beam is held over one region of the sample, referred to as a "spot mode" method.

As described previously, copper has two dominant X-ray emissions, higher energy Cu K (containing Kα and Kβ) X-rays and lower energy Cu L X-rays. In one embodiment of the present invention, the dual X-ray line emission of copper is used to characterize different depths of a copper-containing sample. This is explained by FIGS. 3A–3D, with each figure showing a cross section view of a focused e-beam 301 bombarding the surface of part of an integrated circuit sample 303 that has a copper via 305 surrounded by dielectric material 307. The e-beam trajectory has enough energy to travel through the sample to generate X-rays from the excitation volume 309 of the sample. Each of the four figures shows different scenes from the same e-beam bombardment event of the same sample at the same time.

Figure 3A:
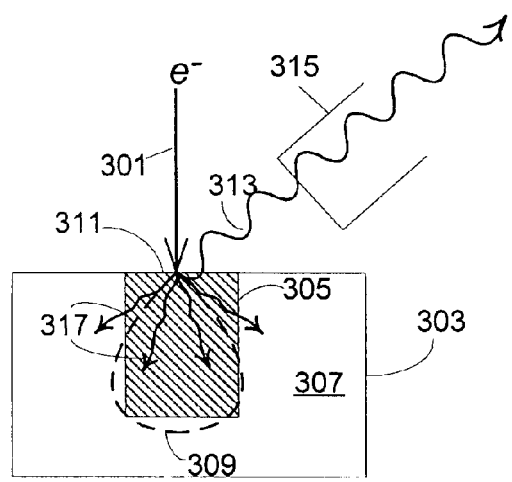
FIG. 3A illustrates a cross section of a semiconductor sample with an electron beam incident upon an upper portion of a recessed conductive region of the specimen, resulting in strong Cu Kα X-ray emission from the sample surface.
Figure 3B:
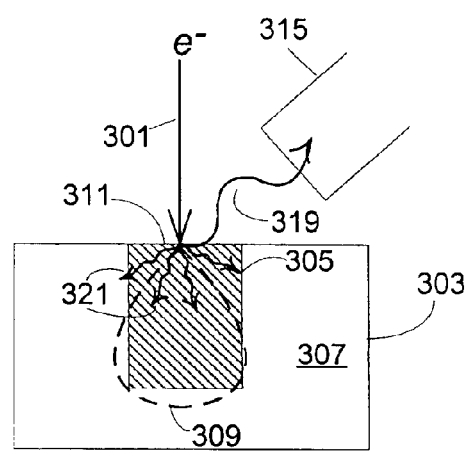
FIG. 3B illustrates a cross section of a semiconductor sample with an electron beam incident upon an upper portion of a recessed conductive region of the specimen, resulting in strong Cu Lα X-ray emission from the sample surface.

FIGS. 3A and 3B depict X-rays emitted from the surface of the sample 311. FIG. 3A shows how Cu Kα X-rays are radiated from the surface of the sample 311. Since the X-rays radiate from all directions within the sample, some Cu Kα X-rays 317 get scattered within the sample, while other Cu Kα X-rays 313 radiate from the surface and get detected by a detector 315. FIG. 3B shows how Cu Lα X-rays are radiated from the surface of the sample 311. Cu Lα X-rays have less energy than Cu Kα X-rays, so the Cu Lα X-rays are more likely to be scattered, such as Cu Lα X-rays 321, and be absorbed by the sample more than Cu Kα X-rays. However, since the X-rays are also radiating from close to the surface of the sample 311, some Cu Lα X-rays 319 are able to radiate unimpeded from the surface and get detected by the detector 315.

Figure 3C:
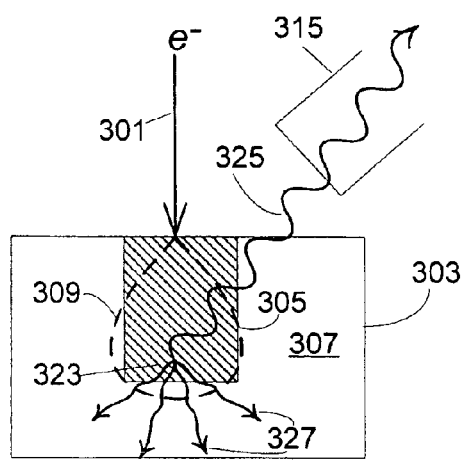
FIG. 3C illustrates a cross section of a semiconductor sample with an electron beam incident upon a lower portion of a recessed conductive region of the specimen, resulting in some Cu Kα X-ray emission from the sample surface.
Figure 3D:
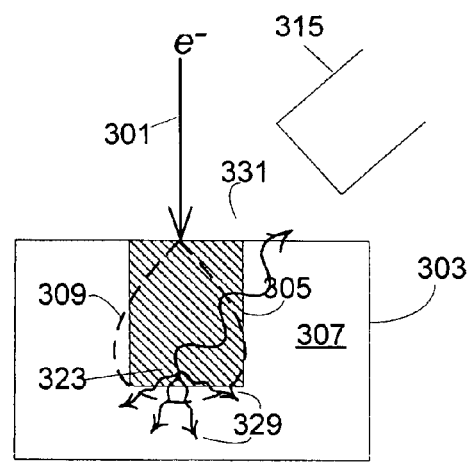
FIG. 3D illustrates a cross section of a semiconductor sample with an electron beam incident upon a lower portion of a recessed conductive region of the specimen, resulting in very little Cu Lα X-ray emission from the sample surface.

FIGS. 3C and 3D depict X-rays emitted from the lower portion of the sample volume 323. FIG. 3C shows how Cu Kα X-rays are radiated from the lower portion of the sample volume 323. As in FIG. 3A, the X-rays radiate from all directions within the sample and some of the Cu Kα X-rays 327 get scattered within the sample. Since the X-rays are radiating from lower within the sample, more of the Cu Kα X-rays 327 are absorbed by the sample and get scattered within the sample, thereby letting less Cu Kα X-rays 325 to emerge from within the sample to get detected by the detector 315, compared to the Cu Kα X-rays from the surface of the sample 311 (depicted in FIG. 3A). FIG. 3D shows how Cu Lα X-rays are radiated from the lower portion of the sample volume 323. Cu Lα X-rays have less energy than Cu Kα X-rays, so the Cu Lα X-rays (e.g., 329) are more likely to be scattered and be absorbed by the sample than the Cu Kα X-rays; Since the Cu Lα X-rays are radiating deep within the lower portion of the volume 323, there are fewer Cu Lα X-rays that can emerge, such as X-rays 331, compared to Cu Lα X-rays that can emerge (such as X-rays 319 of FIG. 3B) from the surface of the sample 311. This means that relatively more of the Cu Lα X-rays are absorbed by the sample at deeper emission depths than Cu Kα X-rays.

Figure 7:
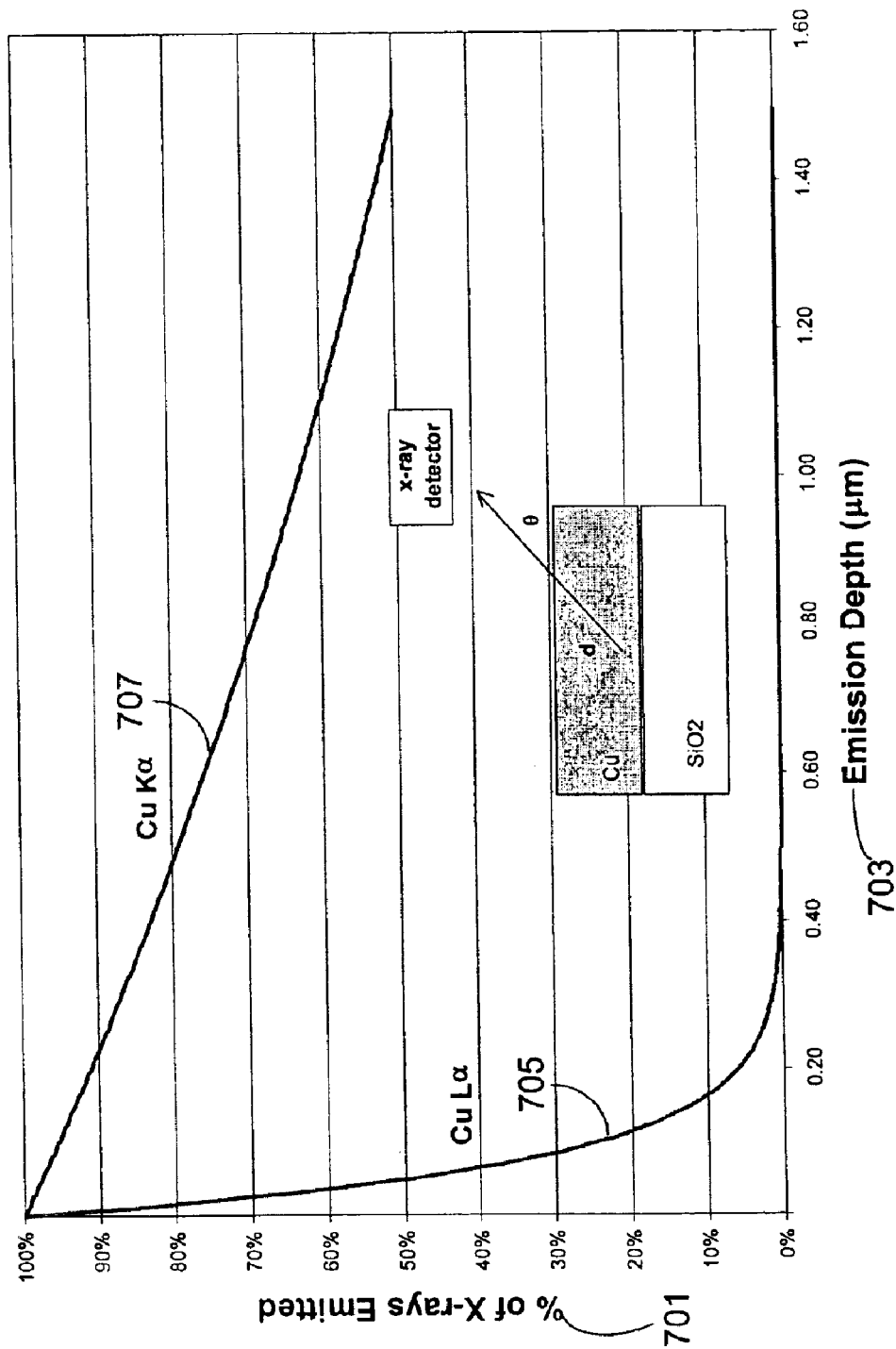
FIG. 7 is a line graph showing the percent of Cu Kα and Cu Lα X-ray emissions as a function of emission depth within a sample.

This difference in absorption of the two types of copper X-rays within copper is illustrated in the graph of FIG. 7. The figure illustrates the percentage of X-rays emitted 701 (vertical axis) with respect to emission depth 703 (horizontal axis) in micrometers ($\mu$m) within a copper on silicon oxide stack. This percentage of emitted X-rays is normalized to the total amount of generated X-ray signals from the sample. FIG. 7 shows the emitted X-ray as detected from an X-ray detector at a take-off angle of 30 degrees with respect to the sample surface. The line for Cu Lα X-ray emission line 705 shows exponential decay with increased emission depth, with substantially no emissions detected by 0.50 $\mu$m sample depth. The line for Cu Kα X-ray emission line 707 shows a less dramatic and more linear decay than the Cu Lα X-ray emission.

As stated previously, a typical application of the present invention is the analysis/characterization of vias and contacts within metal interconnect structures. In a preferred embodiment, the metal interconnect structures are copper lines, vias and contacts within an integrated circuit. A description of how to analyze and characterize different types of voids in copper integrated circuits will be discussed in detail further below.

In alternative embodiments, one can analyze voids in structures composed of other metals such as aluminum, tungsten, tantalum, titanium and chromium, as well as non-metals such as silicon, silicon dioxide, polyimide, suicides and low k insulation materials. In other embodiments, other potentially defective areas such as physical shorts, particles or chemical impurities can be analyzed and characterized. In other embodiments, the present techniques can be used to analyze the localized film thickness variations of one or more layers of material in a film stack. For example, the present techniques can be used to analyze the presence of and amount of dishing and erosion phenomenon occurring as a result of imperfect CMP processes on metal films.

Characterizing Voids in Copper Interconnects

As discussed previously, the emission of Cu K and Cu L from copper can be used to characterize different depths of a copper-containing sample. This characterization of copper material with respect to depth can be used to detect the presence of voids and to characterize the qualities, locations and sizes of the voids. Some techniques for doing this are described below.

Void characterization of Cu interconnect structure can primarily be based on the following emissions: low energy Cu Lα X-rays, high energy Cu Kα X-rays and Si Kα X-rays. As described previously, the low energy Cu Lα X-rays are most strongly detected when they are emitted from the sample surface or upper portion of the sample and decrease dramatically when emitted from deeper regions of the sample. The high energy Cu Kα X-rays are strongly detected when they are emitted from the sample surface and also when they are emitted from deeper bulk portions of the sample.

So if a void were to exist near the sample surface, there is less copper material near the sample surface to emit both Cu Lα X-ray and Cu Kα X-rays. However, the relative amount of Cu Lα X-ray emission will decrease more than the amount of Cu Kα X-ray emission. Likewise, if a void were to exist in the deeper portions of the sample, there is less copper material in the deeper portions of the sample to emit both types of X-rays. In this case, there are already only small amounts of Cu Lα X-ray emission and the relative decrease of the Cu Kα X-ray emission is more dramatic. So detection of Cu Lα X-rays may be used to characterize the upper portions of the sample while detection of Cu Kα X-rays may be used to characterize the deeper portions of the sample. By taking the ratio of detected Cu Lα X-ray emission with respect to Cu Kα X-ray emission of a sample region, one can determine whether the void is near the surface of the sample.

In addition to copper X-rays, Si Kα X-rays will be emitted from the silicon dioxide surrounding the copper interconnects of the integrated circuit. Detection of Si Kα X-rays may be used to emphasize the variations of the Cu Lα X-rays and Cu Kα X-rays with respect to the surroundings. So one can determine more reliable information if a ratio of detected Cu Lα X-ray and Cu Kα X-ray emissions are taken with respect to Si Kα X-ray emission.

This ratio data can be used to help determine the presence of a void(s), as well as the size, distribution and location of the void(s). This is accomplished by analyzing a substantially void-free sample, saving the X-ray emissions data (i.e. different X-ray emissions ratios), and comparing it to a sample with a void(s).

Figure 8:
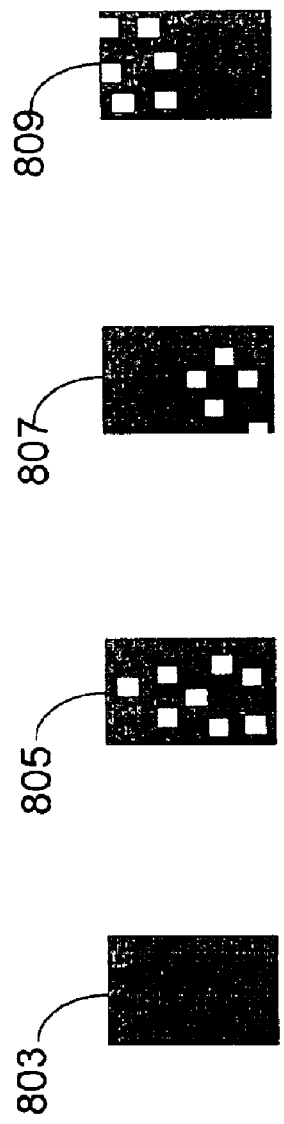
FIG. 8 shows cross section views of copper trenches containing voids in different locations within the trenches and a corresponding table showing the effects of the different void locations on various Cu Lα, Cu Kα and Si Kα ratios.

This ratio comparison technique is described further in the table and drawings in FIG. 8. The figure shows cross section drawings of four different types of copper trenches: one with no substantial voids ("no void") 803, and three with a number of voids distributed differently within the trench. Trench 805 has a number of voids uniformly distributed within the trench ("uniform voids"). Trench 807 has a number of voids distributed in deeper regions of the trench ("deep voids"). Trench 809 has a number of voids distributed in upper regions of the trench ("surface voids"). Silicon dioxide insulator surrounds all the copper trenches. A table 801 below the drawings lists the predicted change in X-ray ratios (Cu Lα/Si Kα, Cu Kα/Si Kα and Cu Lα/Cu Kα) for each of the four types of voided samples. These ratio changes assume full excitation of the trench areas.

The table 801 can be used to help characterize the voids of the unknown sample as being one of the three different types of voided copper trenches. For example, the Cu Lα/ Si Kα and Cu Kα/Si Kα ratio listings for the "uniform voids" are marked as "<<", which indicate a predicted or determined large decrease in the Cu Lα/Si Kα and Cu Kα/Si Kα ratios compared to the "no void" trench. The Cu Kα/Cu Kα ratio listing for the "uniform voids" is marked as "=", which indicates there is no change predicted in the Cu Lα/Cu Kα ratio compared to the "no void" trench. Each of the other types of voided trenches in the table can be interpreted similarly, thereby enabling one to characterize the voids that exist in a sample in which the X-ray ratios have been measured. Note that for the "no void" trench 803, all the ratios are marked as "=" since this is the trench that is used as a reference for distinguishing the three other types of trenches.

Figure 9:
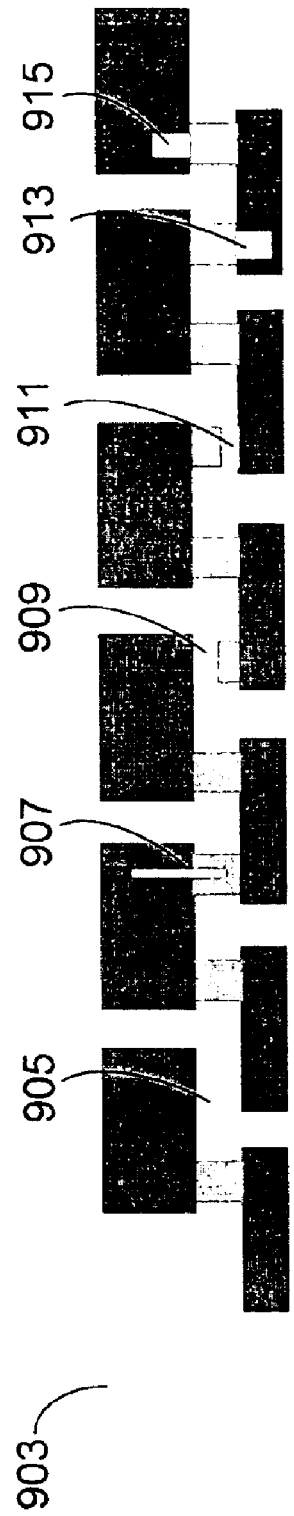
FIG. 9 shows cross section views of different types of voids in complex interconnect copper structures and a corresponding table showing the effects of the different void types on various Cu Lα, Cu Kα and Si Kα ratios.

FIG. 9 shows a table 901 listing Cu Lα/Si Kα, Cu Kα/Si Kα and Cu Lα/Cu Kα ratios for voids within more complex types of interconnect structures compared to the simple trench voids in FIG. 8. Drawing 903 shows an interconnect structure with regions of different types of voids. There are six listed complex voided structures in table 901: "missing via" (depicted as 905), "slit void" or "uniform void" (depicted as 907), "partial via top void" (depicted as 909), "partial via bottom void" (depicted as 911), "trench void bottom" (depicted as 913) and "trench void top" (depicted as 915). Table 901 lists the predicted change in X-ray ratios (Cu Lα/Si Kα, Cu Kα/Si Kα and Cu Lα/Cu Kα) for each of these six types of voided samples and can enable one to characterize the voids that exist in a sample in which the X-ray ratios have been measured.

Example Analysis Process

Now that techniques have described for how to use copper X-ray emission to help determine the size, distribution and location of voids in a sample, reference will be made to an embodiment of a process flow employing these techniques to analyze a target semiconductor device. More specifically, the techniques are applied to analyzing a semiconductor device with copper interconnects and silicon dioxide insulator. One process flow is summarized in the flowcharts of FIGS. 1A through 1C.

Figure 4:
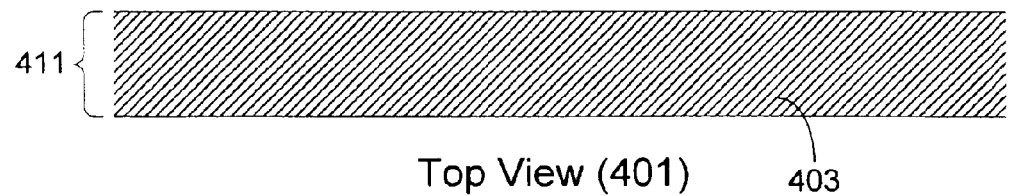
FIG. 4 illustrates one top view and two side views of a semiconductor sample containing copper lines and vias and shows some dimensional parameters of the interconnect structure.
Figure 4:
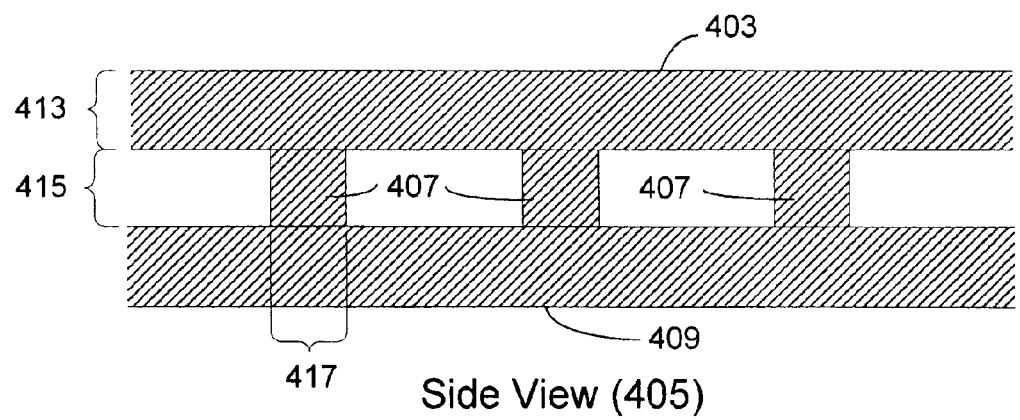
Figure 4:
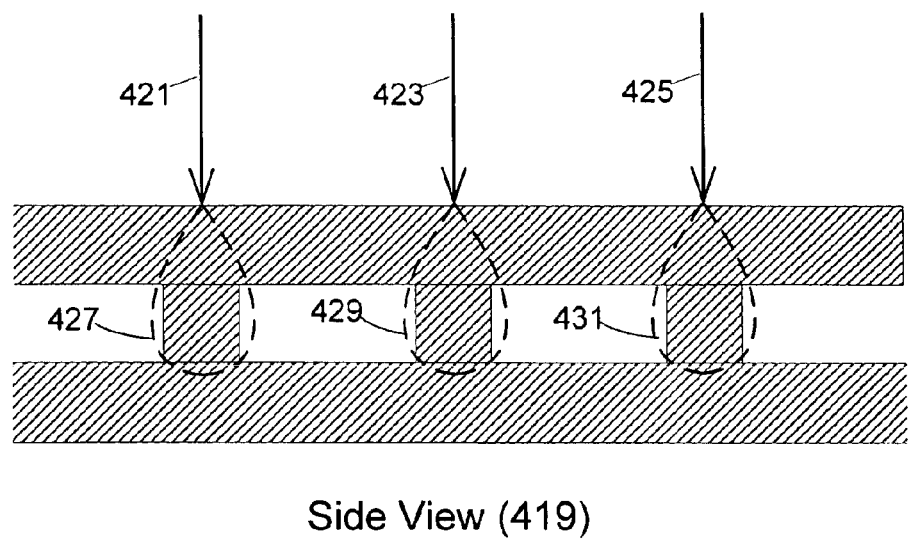

Initially, a "setup" procedure is performed in operation 101. The setup procedure includes identifying a structure of interest. The structure of interest is generally defined as the region of metal interconnect that is to be analyzed and characterized for voids, such as a trench, via, contact pad or part of a line. The structure of interest may be defined in any suitable manner to facilitate activation of such structure of interest with a charged particle beam, such as an e-beam. In one example, the structure of interest is defined with a set of parameters. For example, if the structure of interest is a via, parameters may be copper thickness, via height, and via diameter. See FIG. 4. In this figure, a top view 401 of a copper line 403 is shown and a side view 405 of the same copper line showing vias 407 connecting the upper copper line 403 to copper lines 409 of the next lower metalization layer. In this example, the structure of interest is the area above and around each of the copper vias 407. The parameters for this example may include the top copper line width 411, the copper line thickness 413, the via height 415 and the via diameter 417.

View 419 shows the same perspective of the structure as 405, but showing repeated e-beam sampling directed at these structures of interest at different sampling time intervals (421, 423 and 425). The resulting teardrop shaped electron interaction volumes (427, 429 and 431, respectively) are shown. These electron interaction volumes are the regions that will emit X-rays.

The setup procedure (FIG. 1A, block 101) also includes establishing a set of irradiation parameters, i.e. the scanning parameters if the e-beam is scanned over the sample or e-beam position if the tool is in spot mode. That is, a predefined set of operating conditions of the tool (e.g., e-beam tool) is established for irradiating the structure of interest. In one implementation, the irradiation parameters include an e-beam irradiation area or pattern, e-beam energy, e-beam current, and irradiation duration. The e-beam irradiation condition should be optimized according to the structure of interest and the feature information to be extracted. That is, different scan parameters can be used for the same structure, depending what information is to be obtained. For example, lower incident beam energy may be used if a void is near the surface and a higher beam energy may be used if a void is buried deep is within the structure of interest.

Figure 1A:
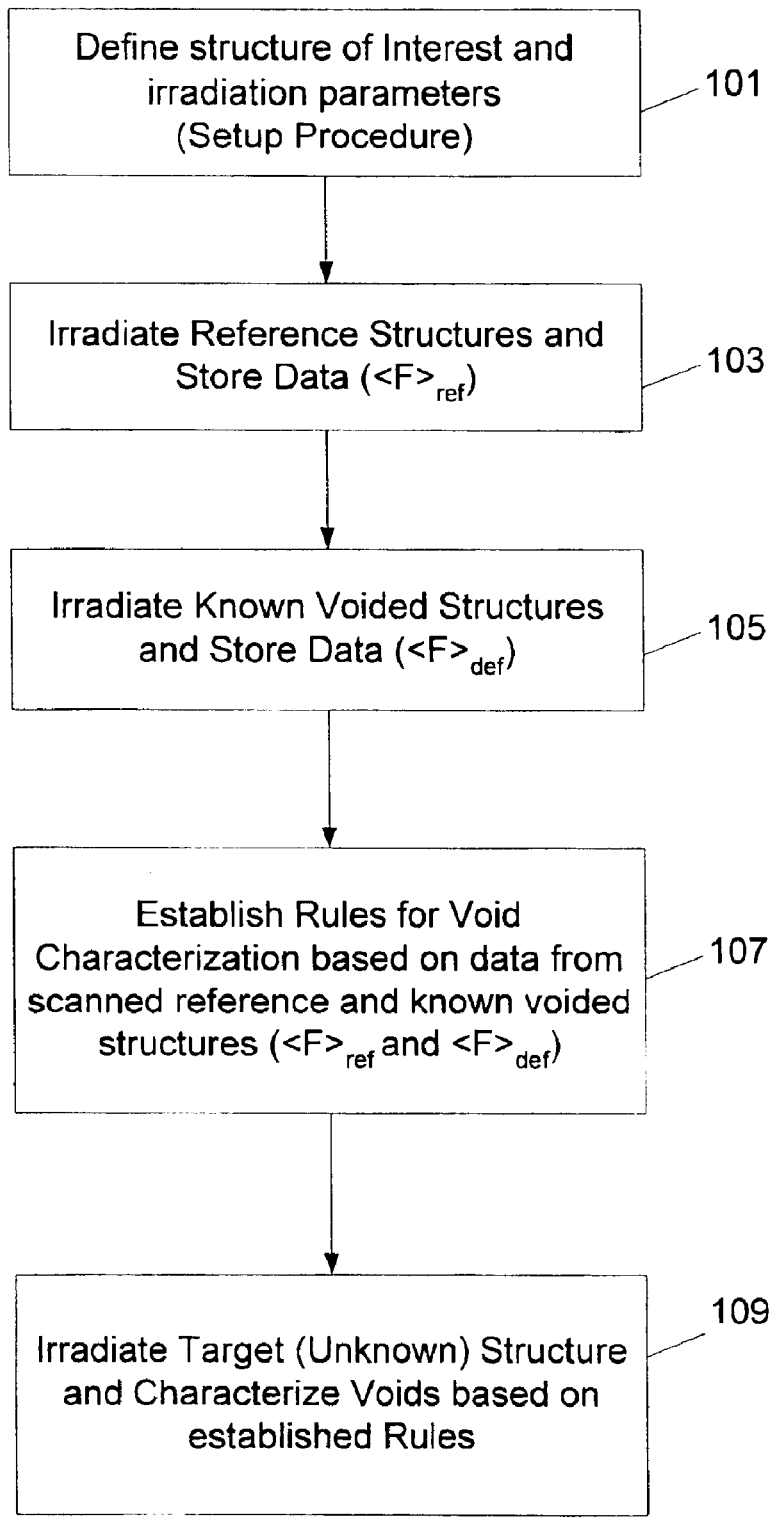
FIG. 1A is a flowchart illustrating a procedure for characterizing voids in conductive interconnect structures of a semiconductor devices in accordance with one embodiment of the present invention.

Referring back to the flowchart FIG. 1A, the next process block 103 includes irradiating reference structures with electron beam and storing the reference structure X-ray data (reference feature vector, $<F>_{ref}$) into a database. A reference structure is a "good" structure of interest in that, ideally, it has substantially no voids. It is the structure to which other sample structures of interest are compared. The $<F>_{ref}$ may have any suitable format for facilitating characterization of the X-ray spectral data obtained from the multiple reference structures. In one embodiment, the $<F>_{ref}$ for a plurality of irradiated reference copper structures includes the following parameters: the mean of the absolute X-ray counts for Cu Kα, the mean of the absolute X-ray counts of Cu Lα, the mean of the absolute X-ray counts of Cu total (includes Cu Kα, CuKβ and CuLα), the mean of the absolute X-ray counts of Si Kα, the mean of the ratios of Cu Lα/Cu Kα, the mean of the ratios of CuTotal/Si Kα, the mean of the ratios of Cu Lα/Si Kα, and the standard deviations of the proceeding absolute and ratio X-ray counts. The $<F>_{ref}$ values will vary for each type of structure of interest. For example, the $<F>_{ref}$ for a copper via will differ from the $<F>_{ref}$ of a copper trench.

One method of obtaining the $<F>_{ref}$ is by irradiating a sample using e-beam techniques described previously. The electron irradiation may be done by scanning an e-beam (typically rastered) or irradiating a single spot (spot mode) over the area of the reference structure, detecting the X-ray emission data and storing it into an analysis or processor unit. To ensure that a reliable $<F>_{ref}$ is calculated, it is preferable that a sufficient amount of multiple measurements of the same reference structures are taken so that X-ray emission data can be averaged and standard deviations can be calculated. Preferably, the $<F>_{ref}$ is calculated from a mean of number of measurements at different locations but with the same structures sufficient. Each measurement may contain multiple raster scans over a certain acquisition time. Furthermore, the ratios of the X-ray emission data are preferred to the absolute intensity for each elemental species. This is because ratios are generally more reliable than the absolute X-ray emission intensity. While the absolute intensity of each element is subject to current and detector efficiency fluctuation, X-ray intensity ratios of two elements is not. Additionally, the scan parameters (e.g., landing energy, scan area, beam current density, etc) established in operation 101 are set for each reference scan to minimize differences due to variable operating conditions.

Figure 10:
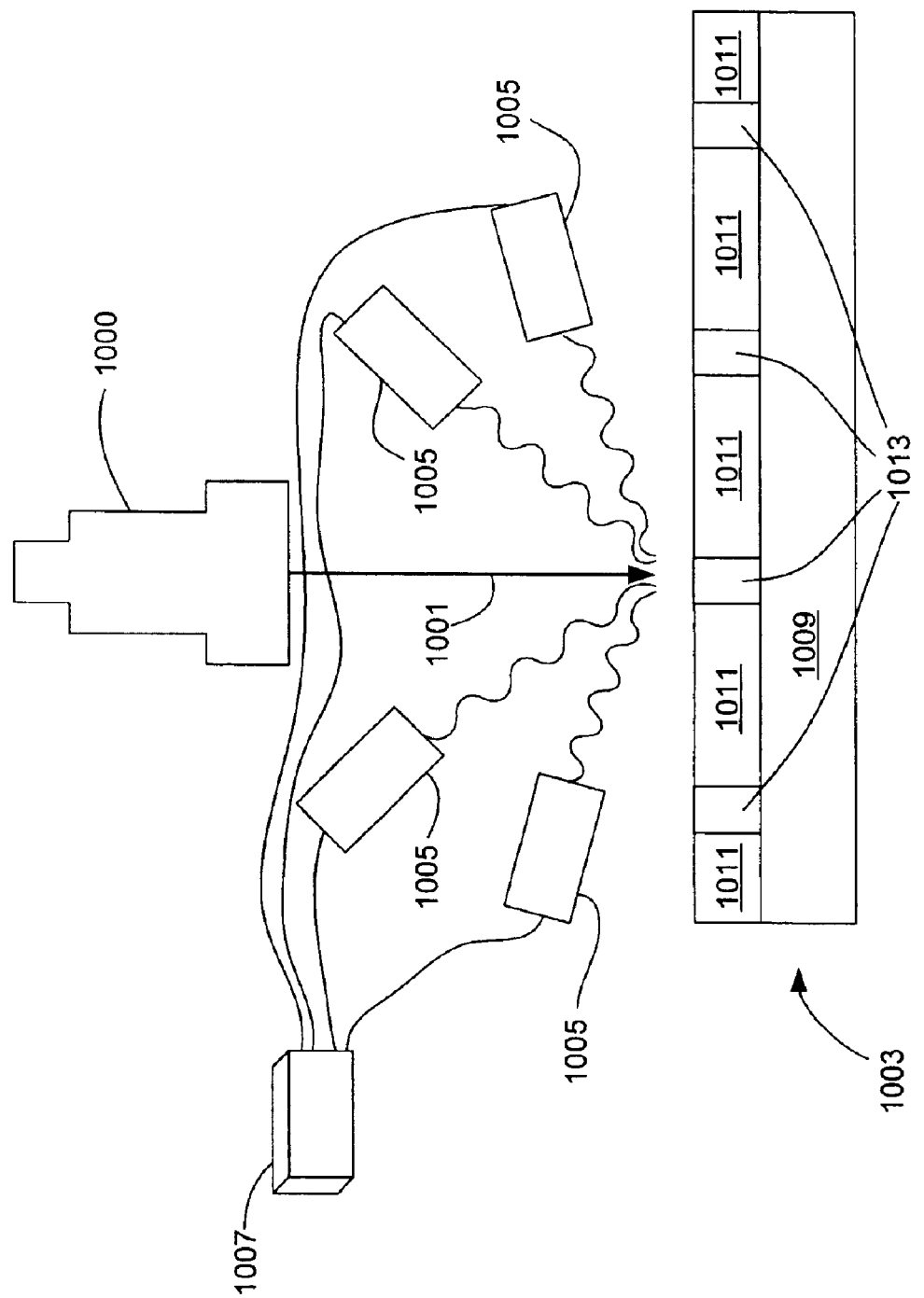
FIG. 10 illustrates an electron beam induced X-ray microanalysis test system according to one embodiment of the present invention.

Any suitable electron beam induced X-ray microanalysis system may be utilized to practice and/or implement the techniques of the present invention. An eV300 automated e-Beam wafer review system available from KLA-Tencor Corporation of San Jose, Calif. may be used. FIG. 10 is a diagrammatic representation of a system utilizing an electron beam induced X-ray microanalysis test system according to one embodiment of the present invention. The system represented in FIG. 10 includes a beam generator 1000, which directs an e-beam 1001 at the sample 1003. The sample 1003 in the example depicted in FIG. 10 is a semiconductor wafer having a silicon substrate 1009 upon which a silicon dioxide layer 1011 is patterned with a plurality of trenches 1013 filled with copper. Before directing e-beam 1001 to sample 1003 and collecting X-ray data, the locations of the structures of interest are established by using standard imaging techniques. In preferred embodiments, the beam spot size is small enough during imaging for resolving the structures of interest. The structures of interests can be irradiated by using a raster scan or by switching to spot mode to acquire x-ray data. In spot mode, the beam spot size may be different from the spot size of raster scan. Furthermore, the beam spot size can be varied.

At least one X-ray detector is used to collect the X-rays emitted from the surface of the sample. The system in FIG. 10 includes four X-ray detectors 1005 positioned above the sample. Any suitable number and type of detector for measuring X-rays at specific energy levels may be utilized. One type of detector is an Energy Dispersive X-ray spectrometer (EDX) system, which collects photons in a wide spectrum of energies. EDX systems are capable of collecting a greater range of signals. As a result however, EDX detectors also collect photons having energies surrounding the characteristic photon energies. This causes EDX detectors to have lower signal to noise ratios. Another type of detector is a wavelength dispersive system (WDS) X-ray detector. Several suitable embodiments of WDS X-ray detectors are described further in co-pending U.S. patent application Ser. No. 09/695,726, filed 23 Oct. 2000, which application is incorporated herein by reference in its entirety.

In the system depicted in FIG. 10, each of the X-ray detectors is coupled with an analysis or processor unit 1007. The analysis/processor unit 1007 can be configured to analyze the data collected by the X-ray detectors 1005 to generate X-ray ratio data of the elemental species in the sample, such as the Cu Lα/Si Kα, Cu Kα/Si Kα and Cu Lα/Cu Kα described previously. The analysis/processor unit 1007 may take the form of any suitable processing or computing system, such as a workstation.

Another method of obtaining the reference vector ($<F>_{ref}$) is by generating simulated data, which does not require actual scanning of samples. Simulated data can be calculated by statistical methods to generate a predicted $<F>_{ref}$. Modifying data from previously scanned "real" data from similar reference structures can also be used to approximate a predicted $<F>_{ref}$. The $<F>_{ref}$ can also be obtained by using a combination of simulated and "real" data.

Referring back to the flowchart FIG. 1A, the next process block 105 includes scanning structures known to contain void(s) and storing this known voided structure X-ray data into the database. These known voided structures have the same parameters as the reference structure. The X-ray data from these scans may then be used to define a defective feature vector ($<F>_{def}$). The $<F>_{def}$ values will vary for each type of void(s) present in the structure. As with the reference structure data, it is preferable that a sufficient amount of scans of voided structures are taken so that X-ray emission data can be averaged and standard deviations can be calculated. The $<F>_{def}$ preferably includes the same parameters as the $<F>_{ref}$, for example, as described above with respect to operation 103. The $<F>_{ref}$ is preferably calculated from measurements with good signal-to-noise ratio. Furthermore, to take out variations in differences of the e-beam condition such as beam energy and beam current that occur at each measurement, it is preferable to use ratios of the X-ray emission data for each elemental species. Additionally, the same scan parameters (e.g., landing energy, scan area, beam current density, etc) established in step 101 are set for each known-voided scan, as well as each reference scan. Like $<F>_{ref}$, the $<F>_{def}$ data is stored in the analysis or processor unit described previously.

Figure 1B:
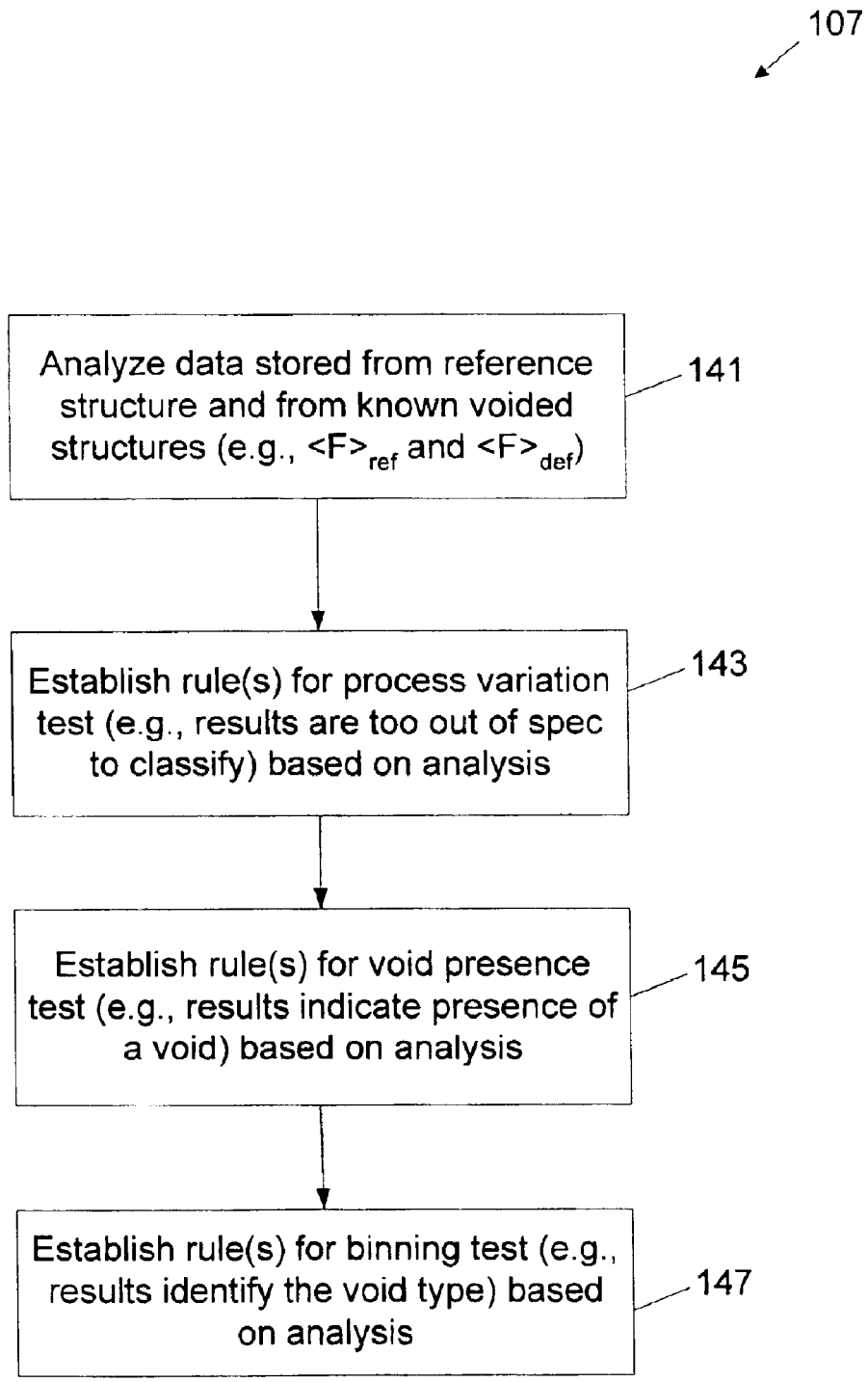
FIG. 1B is a flowchart illustrating the operation of FIG. 1A of establishing rules for the characterization of voids in accordance with one embodiment of the present invention.

The next process block 107 in the flowchart of FIG. 1A includes establishing rules for the characterization of voids based on the stored data obtained from the irradiated reference and known-voided structures (e.g., $<F>_{ref}$ and $<F>_{def}$). FIG. 1B is a flowchart illustrating the details of,block 107, FIG. 1A in accordance with one embodiment of the present invention. Initially, the data that was stored from the reference and known voided structures (e.g., $<F>_{ref}$ and $<F>_{def}$) are analyzed in operation 141. The following operations 143, 145, and 147 may be performed in any suitable order. In the illustrated embodiment, in block 143 rules for a "Process Variation Test" or PVT rules are established based on this data analysis. PVT rules are established for later determining whether an unknown structure has X-ray data that is so out of specification that the unknown structure cannot be characterized. In other words, an unknown structure may deviate so far from the design data that the X-ray data from such structure cannot be further analyzed to determine whether the structure has a void.

In general terms, the X-ray data from the reference and known-void data is analyzed to determine an acceptable range for X-ray data obtained. for an unknown voided structure. For instance, one method for determining process variation involves evaluating Figures of Merit that describe how much variation exists in collected data sets. These Figures of Merit are often referred to as Process Variation Test Figures of Merit, or PVT Figures of Merit. One method of defining PVT Figures of Merit is to calculate the coefficient of variation using the data sets obtained for the same structure but over multiple locations on the wafer. Typical values of Figures of Merit for normal process variation within process control can be determined experimentally for each layer of the sample. The typical values can be set as default thresholds to distinguish between normal process variation and out-of-control process variations.

After the PVT rules are established, rules for determining the presence or "localization" of a void within an unknown structure may then be established based on the analysis of the data from the reference and/or known voided structures in operation 145. Such rules are referred to herein as "Defect Localization Test" or DLT rules. The DLT rules may be established in any suitable manner. In some embodiments, DLT rules are determined using a combination of experimental data, theoretical analyses, and computational modeling. For instance, it may be determined that if the X-ray absolute count or ratio data from an unknown voided structure is within a predefined range, a void is present within such structure. The range may be determined experimentally. In one implementation, a reasonable initial rule (e.g., as listed below) may be determined and then verified by inspecting a plurality of known voided structures to determine whether this rule reliably classifies each known voided structure as having a void. An example set of DLT rules may include:

if any or a specified subset of the mean X-ray count or ratio value from the unknown structure is more than two standard deviations (e.g., as obtained from the feature vector of the reference structures) from the corresponding X-ray count or ratio value from the reference structure, the unknown structure is characterized as having a void (Note that the rule can be tightened by using three or higher standard deviations to provide more sensitivity); and if any or a specified subset of the mean X-ray count or ratio value from the unknown structure is not more than two standard deviations from the corresponding X-ray count or ratio value from the reference structure, the unknown structure is characterized as not having a void.

After the DLT rules are established for the structure of interest, rules for binning or classifying the localized void(s) are established based on the analysis of the X-ray data from the reference and/or known voided structures in operation 147. These rules are referred herein as "Defect Binning Test" or DBT rules. These DBT rules may be determined by analyzing how much particular subset(s) of the X-ray data obtained from the known void structures differ from corresponding data from the reference structures. The tables of FIGS. 8 and 9 represent reference and known-voided data obtained from trench type structures and from complex type structures, respectively. Note that these tables are shown as exemplary methods for classifying voids using an example set of DLT rules and are not meant to limit the invention to any particular method or DLT rules. In FIGS. 8 and 9, the following symbols are defined as follows:

| Symbol | Description | Definition |
|---|---|---|
| << | "much less than" | Unknown structure ratio is more than seven standard deviations less than reference structures ratio. |
| < | "less than" | Unknown structure ratio is more than four but less than seven standard deviations less than reference structures ratio. |
| ≦ | "somewhat less than" | Unknown structure ratio is more than two but less than four standard deviations less than reference structures ratio. |
| = | "equal to" | Unknown structure ratio is less than two standard deviations greater or less than reference structures ratio. |
| ≧ | "somewhat greater than" | Unknown structure ratio is more than two but less than four standard deviations greater than reference structures ratio. |
| > | "greater than" | Unknown structure ratio is more than four but less than seven standard deviations greater than reference structures ratio. |
| >> | "much greater than" | Unknown structure ratio is more than seven standard deviations greater than reference structures ratio. |

Therefore, by using the rules indicated in the tables of FIGS. 8 and 9, one could characterize voids within different types of samples. For example, referring to the table 801 of FIG. 8, the following example rules may be established for characterizing unknown voided trench type structures:

if the ratios of CuLα/SiKα obtained from an unknown structure is "much less than" (more than seven standard deviations less than) the corresponding ratio of CuLα/SiKα obtained from the reference structure AND if the ratio of CuKα/SiKα obtained from an unknown structure is "much less than" the corresponding ratio of CuKα/SiKα obtained from the reference structure AND if the ratio of CuLα/CuKα obtained from an unknown structure is "equal to" (within two standard deviations) the corresponding ratio of CuLα/CuKα obtained from the reference structure, the unknown trench structure contains uniform voids 805;

if the ratio of CuLα/SiKα obtained from an unknown structure is "equal to" the corresponding ratio of CuLα/SiKα obtained from the reference structure AND if the ratio of CuKα/SiKα obtained from an unknown structure is "much less than" the corresponding ratio of CuKα/SiKα obtained from the reference structure AND if the ratio of CuLα/CuKα obtained from an unknown structure is "much greater than" (more than seven standard deviations greater than) the corresponding ratio of CuLα/CuKα obtained from the reference structure, the unknown trench structure contains deep voids 807; and if the ratio of CuLα/SiKα obtained from an unknown structure is "much less than" the corresponding ratio of CuLα/SiKα obtained from the reference structure AND if the ratio of CuKα/SiKα obtained from an unknown structure is "somewhat less than" (more than two but less than four standard deviations less than) the corresponding ratio of CuKα/SiKα obtained from the reference structure AND if the ratio of CuLα/CuKα obtained from an unknown structure is "less than" (more than four but less than seven standard deviations less than) the corresponding ratio of CuLα/CuKα obtained from the reference structure, the unknown trench structure contains uniform voids 809.

Note that these rules may vary depending on the structure that is being inspected. Of course, any suitable number and type of rules may be generated from the table 801 of FIG. 8. DBT rules may similarly be generated for complex structures. For example, referring to the table 901 of FIG. 9, the following example rules may be established for characterizing unknown voided complex type structures:

if the ratio of CuLα/SiKα obtained from an unknown structure is "much less than" than the corresponding ratio of CuLα/SiKα obtained from the reference structure AND if the ratio of CuKα/SiKα obtained from an unknown structure is "much less than" the corresponding ratio of CuKα/SiKα obtained from the reference structure AND if the ratio of CuLα/CuKα obtained from an unknown structure is "somewhat less than" the corresponding ratio of CuLα/CuKα obtained from the reference structure, the unknown trench structure contains a missing via type void 905; if the ratio of CuLα/SiKα obtained from an unknown structure is "much less than" the corresponding ratio of CuLα/SiKα obtained from the reference structure AND if the ratio of CuKα/SiKα obtained from an unknown structure is "less than" the corresponding ratio of CuKα/SiKα obtained from the reference structure AND if the ratio of CuLα/CuKα obtained from an unknown structure is "less than" the corresponding ratio of CuLα/CuKα obtained from the reference structure, the unknown trench structure contains a top portion partial via type void 909; and if the ratio of CuLα/SiKα obtained from an unknown structure is "much less than" the corresponding ratio of CuLα/SiKα obtained from the reference structure AND if the ratio of CuKα/SiKα obtained from an unknown structure is "less than" the corresponding ratio of CuK/SiK obtained from the reference structure AND if the ratio of CuLα/CuKα obtained from an unknown structure is "much less than" the corresponding ratio of CuLα/CuKα obtained from the reference structure, the unknown trench structure contains a top portion trench type void 915.

Figure 1C:
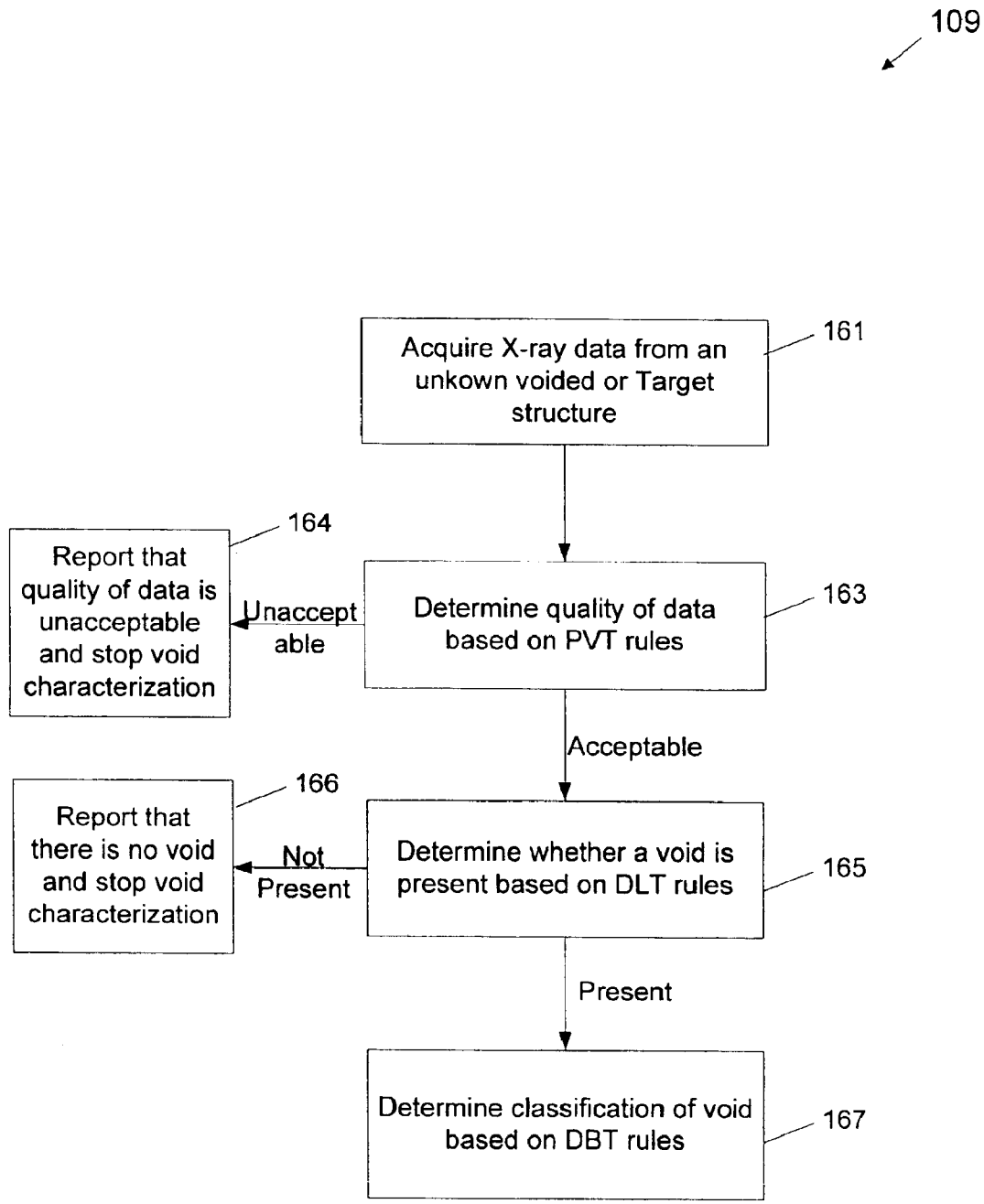
FIG. 1C outlines a procedure for characterizing voids of a target structure based on a set of rules established by analyzing X-ray data taken from a plurality of reference structures and known voided structures in accordance with one embodiment of the present invention.

Referring back to FIG. 1A, the next process block 109 includes scanning a target (unknown) structure and characterizing the voids in the target structure based on the established rules. FIG. 1C outlines a procedure for characterizing a target structure based on the established rules in accordance with one embodiment of the present invention. First in operation 161, a target structure is scanned to obtain X-ray data corresponding to at least a portion of the data collected for the reference and known voided structures. For example, absolute X-ray counts and ratios are obtained for CuLα, CuKα, and SiKα. Of course, the type of X-ray data obtained will vary with the composition of the target structure.

It is then determined whether the quality of the data obtained from the target structure is acceptable based on the established PVT rules in operation 163. In some specific examples, the dividing line separating acceptable from unacceptable data are set to between about 0.03 to 0.05, depending on the feature (Figures of Merit) being inspected. If it is determined and reported that the data is unacceptable and the process variation is too high, the void characterization process 109 is halted in operation 164. In other words, the X-ray data from the target structure is too out of specification to characterize further (e.g., determine whether a void is present and classify such void if found). The data and/or target structure may then be further inspected to determine why the data is so out of range.

If it is unknown whether the scanned area contains voids, a Suspect Outlier Test can be conducted to find the outlier among the data set for the purpose of accurate defect localization. This test can be done by using any suitable standard outlier test method or statistics. Once an outlier is identified, the data associated with this outlier will not be used in the calculation of PVT Figures of Merit to evaluate the data scattering and process variation. If the purpose is to evaluate the data scattering and process variation without need to identify the exact void presence, then PVT Figures of Merit can be calculated over all the data.

If the data is acceptable, it is then determined whether a void is present based on the established DLT rules in operation 165. The localization of void is based on the Figures of Merit calculated for DLT and the rules of DLT. In one embodiment, using the above described sample DLT rules, it may be determined that there is no void present when any or a specified subset of the mean X-ray count or ratio value from the unknown structure is not more than 2 standard deviations from the corresponding X-ray count or ratio value from the reference structure, the target structure is characterized as not having a void. Otherwise, the target structure is characterized as having a void. If a void is not present, it may be reported that a void is not present and the void characterization process 109 is stopped in operation 166.

If there is a void, the found or localized void is then classified based on the DBT rules in operation 167. For example, trench void(s) are classified as one or more uniform void(s), one or more deep void(s), or one or more surface void(s). In another application, complex type structure void(s) are classified as one or more missing via(s), one or more slit or uniform void(s), or one or more partial/top void(s), one or more partial/bottom void(s), one or more trench/top void(s), or one or more trench/bottom void(s). In a specific application using the above example DBT rules, a target trench type structure is characterized as having uniform voids when the ratio of CuαL/SiKα obtained from the target structure is much less (e.g., less than 7 standard deviations) than the ratio of CuLα/SiKα obtained from the reference structure AND when the ratio of CuKα/SiKα obtained from the target structure is much less than the ratio of CuKα/SiKα obtained from the reference structure. After the target structure void(s) are characterized (e.g., qualified as being acceptable to characterize further, located as being present, and classified into a specific void type if present), the characterization process ends.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of determining characteristic X-ray emission data from a certain volume of a certain interconnect structure in a sample, the method comprising:
   directing an electron beam towards the surface of the sample to thereby generate X-rays emitted from the volume of the interconnect structure in the sample;
   detecting the X-rays emitted from the sample; and
   characterizing the distribution and characteristics of one or more voids in the interconnect structure based on the detected X-rays.

2. A method as recited in claim 1, wherein the characterization of the void or voids comprises determining the presence of one or more voids and determining the position or distribution of the void or voids with respect to the interconnect structure when one or more voids are present.

3. A method as recited in claim 1, wherein the sample is a semiconductor device.

4. A method as recited in claim 3, wherein the interconnect structure in the semiconductor device includes at least copper.

5. A method as recited in claim 4, wherein the copper containing interconnect structure in the semiconductor device is at least partially surrounded by dielectric material.

6. A method as recited in claim 4, wherein the detected X-rays are at least copper Kα and copper Lα X-rays.

7. A method as recited in claim 5, wherein the detected X-rays are at least copper Kα, copper Lα and silicon Kα X-rays.

8. A method as recited in claim 1, wherein X-ray emission data is collected from a plurality of similar volumes of similar interconnect structures and statistical data is calculated to determine similar X-ray emission characteristics between the similar volumes of similar interconnect structures.

9. A method as recited in claim 8, wherein X-ray emission data is collected from a plurality of similar volumes of similar interconnect structures in the same sample.

10. A method as recited in claim 8, wherein X-ray emission data is collected from a plurality of similar volumes of similar interconnect structures in different samples.

11. A method as recited in claim 1, wherein the electron beam is focused to a spot size small enough for resolving structures of interest within the sample.

12. A method as recited in claim 11, wherein the electron beam has an energy greater than about 15 keV.

13. A method as recited in claim 11, wherein the electron beam is rastered over an area of the sample surface.

14. A method as recited in claim 1, wherein the volume is a teardrop shaped.

15. A method as recited in claim 1, wherein the volume includes at least a portion of a metal via type structure.

16. A method as recited in claim 1, wherein the volume includes at least a portion of a metal line structure.

17. A method of facilitating the determination of the void characteristics within a conductive interconnect structure of a semiconductor device, the method comprising:

directing a charged particle beam toward a first volume that is at least partially within a first interconnect structure of a first sample containing substantially no voids, to thereby cause the first volume to emit X-rays from the first sample;

directing a charged particle beam toward a second volume that is-at least partially within a second interconnect structure of a second sample containing voids with known void characteristics, to thereby cause the second volume to emit characteristic X-rays from the second sample;

directing a charged particle beam toward a third volume that is at least partially within a third interconnect structure of a third sample with unknown void characteristics, to thereby cause the third volume to emit characteristic X-rays from the third sample, wherein the first, second and third volumes are substantially equal; and determining the void characteristics in the third interconnect structure in the third sample based on a comparison of the X-rays emitted from the first, second, and third samples.

18. A method as recited in claim 17, wherein the void characteristics comprise the location, size, shape and distribution of the void or voids with respect to the interconnect structure.

19. A method as recited in claim 18, wherein the directed charged particle beam for the first, second and third samples is an electron beam.

20. A method as recited in claim 19, wherein the electron beam is focused to a spot size small enough for resolving structures of interest within the sample.

21. A method as recited in claim 20, wherein the electron beam has an energy greater than about 15 keV.

22. A method as recited in claim 21, wherein the electron beam is rastered over an area of the sample surface.

23. A method as recited in claim 17, wherein determining the void characteristics of the third sample include determining a quality of the X-rays emitted from the third sample.

24. A method as recited in claim 23, further comprising reporting that the X-ray emitted from the third sample is unacceptable and halting further characterization of voids of the third sample when the quality of the X-rays emitted from the third sample are determined to be unacceptable.

25. A method as recited in claim 17, wherein determining the void characteristics involve measuring the process variations of the first, second and third samples.

26. A method as recited in claim 17, wherein determining the void characteristics of the third sample includes determining whether one or more voids are present within the third sample.

27. A method as recited in claim 17, wherein X-ray data from a plurality of samples containing substantially no voids are collected so that statistical data can be calculated to determine similar X-ray emission characteristics of samples containing substantially no voids, to be compared to data from the sample with known void characteristics and the sample with unknown void characteristics.

28. A method as recited in claim 27, wherein the statistical data are the mean, standard deviation, absolute value and ratios of the different X-ray intensities.

29. A method as recited in claim 17, wherein X-ray data from a plurality of samples containing known void characteristics are collected so that statistical data can be calculated to determine similar X-ray emission characteristics of samples containing known void characteristics, to be compared to data from the sample containing substantially no voids and the sample with unknown void characteristics.

30. A method as recited in claim 29, wherein the statistical data are the mean, standard deviation, absolute value and ratios of the different X-ray intensities.

31. A method as recited in claim 29, wherein X-ray data from a plurality of samples containing substantially no voids are collected so that statistical data can be calculated to determine similar X-ray emission characteristics of samples containing substantially no voids, to be compared to statistical data from the samples with known void characteristics and the sample with unknown void characteristics.

32. A method as recited in claim 31, wherein the statistical data are the mean, standard deviation, absolute value and ratios of the different X-ray intensities.

33. A method as recited in claim 17, wherein the interconnect structure includes at least copper.

34. A method as recited in claim 33, wherein the detected X-rays are at least copper K$\alpha$ and copper L$\alpha$ X-rays.

35. A method as recited in claim 34, wherein various combinations of ratios of the detected copper K$\alpha$ and copper L$\alpha$ X-rays are used to determine the location of voids within the interconnect structure in the third sample.

36. A method as recited in claim 17, wherein the copper containing interconnect structure is at least partially surrounded by dielectric material.

37. A method as recited in claim 36, wherein the detected X-rays are at least copper K$\alpha$, copper L$\alpha$ and silicon K$\alpha$ X-rays.

38. A method as recited in claim 37, wherein various combinations of ratios of the detected copper K$\alpha$, copper L$\alpha$ X-rays, and silicon K$\alpha$ X-rays are used to determine the location of voids within the interconnect structure in the third sample.

39. A method as recited in claim 17, wherein the directed charged particle beam for the first, second and third samples is a focused ion beam.

40. An apparatus for characterizing a void within an interconnect structure of a semiconductor device, comprising:

a beam generator operable to direct a charged particle beam towards a structure;

a detector positioned to detect X-rays from the structure in response to the charged particle beam; and a processor operable to:

cause the beam generator to direct a charged particle beam towards the structure; and characterize one or more voids of the volume of the interconnect structure based on the detected X-rays.

41. An apparatus as recited in claim 40, wherein the characterizing operation is based on a ratio of a first X-ray intensity for a first material over a second X-ray intensity for a second material, wherein the first and second X-ray intensities are obtained from the detected X-rays from the scanned structure.

42. An apparatus as recited in claim 40, wherein the scanned structure is a portion of a interconnect structure in an integrated circuit device.

43. An apparatus as recited in claim 40, wherein the directed charged particle beam is an electron beam.

44. An apparatus as recited in claim 43, wherein the electron beam is focused to a spot size small enough for resolving structures of interest within the sample.

45. An apparatus as recited in claim 44, wherein the electron beam has an energy greater than about 15 keV.

46. An apparatus as recited in claim 45, wherein the electron beam is rastered over an area of the sample surface.

47. An apparatus as recited in claim 40, wherein the directed charged particle beam for the first, second and third samples is a focused ion beam.

48. An apparatus as recited in claim 40, wherein the processor is further operable to:

cause the beam generator to scan a charged particle beam over a reference portion of an interconnect structure, and wherein a void is characterized by comparing the first ratio from the scanned first via or contact to a second ratio from the scanned reference via, wherein the second ratio is a third X-ray intensity for the first material over a fourth X-ray intensity for the second material, wherein the third and fourth X-ray intensities are obtained from X-rays detected from the scanned reference portion of interconnect structure.

49. An apparatus as recited in claim 40, wherein the processor is further operable to locate the void or voids based on the ratio of the first X-ray intensity for the first material over the second X-ray intensity for the second material.

50. An apparatus as recited in claim 40, wherein the processor is further operable to:

cause the beam generator to scan a charged particle beam over a plurality of second portions of interconnect structures, and wherein characterizing the void or voids of the first portion of interconnect structure is accomplished by determining whether the first ratio from the scanned first portion of interconnect structure significantly differs from a majority of second ratios calculated for the second portions of interconnect structures, wherein the second ratios of the plurality of portions of interconnect structures are each calculated by dividing a third X-ray intensity for the first material by a fourth X-ray intensity for the second material, wherein the third and fourth X-ray intensities are obtained from X-rays detected from each of the scanned second portions of interconnect structures.

51. An apparatus as recited in claim 40, wherein the first and second X-ray intensity are X-ray count values.

52. An apparatus as recited in claim 40, further comprising reporting that the X-ray emitted from the third sample is unacceptable and halting further characterization of voids of the third sample when the quality of the X-rays emitted from the third sample are determined to be unacceptable.

* * * * *

UNITED STATES PATENT AND TRADEMARK OFFICE
CERTIFICATE OF CORRECTION

PATENT NO.    : 6,924,484 B1
DATED         : August 2, 2005
INVENTOR(S)   : Wang et al.

It is certified that error appears in the above-identified patent and that said Letters Patent is hereby corrected as shown below:

Column 7,
Lines 66-67, "suicides and low k" should be -- silicides and low k --.

Signed and Sealed this

Seventh Day of March, 2006

JON W. DUDAS
*Director of the United States Patent and Trademark Office*